(12) United States Patent
Meints et al.

(10) Patent No.: US 8,852,503 B2
(45) Date of Patent: Oct. 7, 2014

(54) METHOD OF BIOLOGICAL SOIL DECONTAMINATION

(75) Inventors: Henk Meints, Smilde (NL); Herman Feil, Ede (NL)

(73) Assignee: Thatchtec B.V., Wageningen (NL)

( * ) Notice: Subject to any disclaimer, the term of this patent is extended or adjusted under 35 U.S.C. 154(b) by 798 days.

(21) Appl. No.: 13/131,894

(22) PCT Filed: Nov. 30, 2009

(86) PCT No.: PCT/NL2009/050724
§ 371 (c)(1),
(2), (4) Date: May 31, 2011

(87) PCT Pub. No.: WO2010/064903
PCT Pub. Date: Jun. 10, 2010

(65) Prior Publication Data
US 2012/0034033 A1    Feb. 9, 2012

(30) Foreign Application Priority Data

Dec. 1, 2008 (NL) .................................... 1036261
Oct. 19, 2009 (NL) .................................... 2003665

(51) Int. Cl.
| | |
|---|---|
| A61L 2/00 | (2006.01) |
| B09C 1/10 | (2006.01) |
| B09C 1/00 | (2006.01) |
| A01N 25/00 | (2006.01) |
| B09C 1/08 | (2006.01) |
| A61L 2/16 | (2006.01) |

(52) U.S. Cl.
CPC . B09C 1/00 (2013.01); A01N 25/00 (2013.01); B09C 1/08 (2013.01); A61L 2/16 (2013.01)
USPC ....................... 422/28; 405/128.1; 405/128.7

(58) Field of Classification Search
USPC ................................ 422/28; 405/128.1, 128.7
See application file for complete search history.

(56) References Cited

U.S. PATENT DOCUMENTS

| | | | |
|---|---|---|---|
| 3,161,497 A | 12/1964 | Amburn | |
| 5,937,572 A | 8/1999 | Neumann | |
| 6,368,019 B2 * | 4/2002 | Sugawa et al. | ............ 405/128.45 |
| 8,137,029 B2 * | 3/2012 | Richter | ....................... 405/128.6 |
| 2008/0047906 A1 | 2/2008 | Zhang | |

FOREIGN PATENT DOCUMENTS

| | | |
|---|---|---|
| GB | A-1440954 | 6/1976 |
| JP | A-2000026207 | 1/2000 |
| WO | WO-A-02/056683 | 7/2002 |

* cited by examiner

Primary Examiner — Sean E Conley
(74) Attorney, Agent, or Firm — Sunit Talapatra; Foley & Lardner LLP

(57) ABSTRACT

A method of biological soil decontamination, including the introduction into the soil of a product that contains a material chosen from a group consisting of proteins, carbohydrates and lipids. The product introduced into the soil does not contain any unprocessed fresh plants or unprocessed fresh plant residues. The method also includes the application of a barrier layer over the soil, e.g., between the soil and the air.

21 Claims, No Drawings

METHOD OF BIOLOGICAL SOIL DECONTAMINATION

CROSS REFERENCE TO PRIOR APPLICATIONS

The present application is a National Stage Application of PCT International Application No. PCT/NL2009/050724 (filed on Nov. 30, 2009), under 35 U.S.C. 371, which claims priority to Netherlands Patent Application No. 2003665 (filed on Oct. 19, 2009) and Netherlands Patent Application No. 1036261 (filed on Dec. 1, 2008), each of which are hereby incorporated by reference in their respective entireties.

FIELD OF THE INVENTION

Embodiments in accordance with the present invention relate to a method of biological soil decontamination.

BACKGROUND

Soil decontamination, aimed at the destruction of harmful organisms in the soil, is often necessary in agriculture. These organisms, notably nematodes, fungi and bacteria, can have an undesirable effect both on the quality and on the quantity of the harvest. Soil decontamination can be carried out in various ways, namely by chemical, physical and biological means, heating being a physical method.

In the case of chemical soil decontamination, which is a conventional way of sterilizing the soil, chemicals that kill the harmful organisms are introduced into the soil. However, chemical soil decontamination has a number of major limitations, notably from the environmental point of view. Since chemicals can directly affect the living environment and/or the farm produce to be grown, their use for chemical soil decontamination is strictly regulated by the requirements for a permit and by the directions for use.

Methyl bromide, a colourless and almost odourless toxic gas, was widely employed for chemical soil decontamination in the past. However, methyl bromide attacks the ozone layer, and its use has been forbidden under the Montreal Protocol since 1 Jan. 2005. Its production should also stop as from 1 Jan. 2015. An alternative soil decontaminating agent is for example 1,3-dichloropropene, but the use of this chemical has also been forbidden in the European Union since March 2008. In the Netherlands, the use of methyl bromide for soil decontamination was made illegal as long ago as 1992. The only permissible alternative—Monam®—is of limited applicability and can only be used at most once every five years.

The use of a product of plant origin for soil decontamination has been described e.g. in WO 02/056683. In this case, allicin—a compound that is liberated when garlic is pressed—is applied to the soil before sowing or planting in order to protect the plants from pathogenic organisms, such as fungi, bacteria, protozoa and nematodes. A drawback of allicin is that it is a chemically unstable volatile compound, so that its large-scale use is impractical; in fact, allicin is most suitable for soil decontamination in small areas or in greenhouses.

In the case of physical soil decontamination, the harmful organisms present in the soil are killed by heating it to 80-90° C., for example by passing steam into the soil or heating the soil with flames. However, the use of steam has the disadvantage of being very costly for use on a large scale, while if flames are used, it is very difficult to achieve a uniform heating of the soil. Quite in general, physical soil decontamination is rather expensive and gives variable results. WO 03/099004 discloses a system and a method for the in situ sterilization of the soil and the destruction of insects and weeds in it. This method consists of exposing the soil down to a specified depth to an energy flux with a microwave frequency so chosen as to dissociate the biopolymers.

Biological soil decontamination (BSC) is an alternative to chemical and physical soil decontamination. In this case, fresh, readily degradable plants or parts of plants, such as grass cuttings are introduced into the soil, and the latter is hermetically covered with a plastic film for some time, generally for 6 weeks. It has been found that this reduces the number of pathogens, such as nematodes and fungi, in the soil. Due to the indirect action of the materials introduced into the soil in the case of biological soil decontamination, none of the plant protection legislation is applicable here.

The use of biological soil decontamination in asparagus cultivation has been described for example in *Plant Life*, 2 (2008), where the authors studied the combating of *Fusarium oxysporum* f. sp. *asparagi* and *Fusarium redolens* f. sp. *asparagi*. Although *fusarium* is not fully destroyed, the asparagus plants planted out in the decontaminated plots seemed to do better. The authors also reported a better quality and a higher yield of asparagus over several years after this biological soil decontamination.

SUMMARY

A number of factors, however, militate against the wider use of the biological soil decontamination described above, for example, the relatively high cost, notably the cost of the plastic film, and the application and removal of this film. As a result, biological soil decontamination is currently only economically feasible in the case of special crops, such as asparagus, where there are no efficient alternatives or only very expensive ones. Another disadvantage lies in the limited time over which biological soil decontamination can be practised. For a sufficiently fast digestion of the fresh organic material that is used in the current approach, the soil temperature must be above a certain minimum value, and furthermore the crop to be ploughed in must itself be grown before the biological soil decontamination. Biological soil decontamination cannot therefore be carried out in the winter or the early spring. Other technical problems concern the design and service life of the plastic film, and damage to it by birds and wildlife, for which reason coverage for the best (sufficiently long) period sometimes cannot be reached. In addition, biological soil decontamination gives variable results, probably because of the variable quality and composition of the crop to be ploughed in.

As can thus be seen, biological soil decontamination based on the use of fresh plants or plant residues has a number of disadvantages. The aim of the present invention is to offer an alternative method of biological soil decontamination that is preferably completely or at least partially free of these disadvantages.

It has now been found surprisingly that remarkably good results can be obtained by a method of biological soil decontamination in which a product including non-living organic material is introduced into the soil and a barrier layer is applied between the soil and the air.

It is also surprising that remarkably good results are obtained by a method of biological soil decontamination in which a product including a material chosen from a group of proteins, carbohydrates and lipids is introduced into the soil and a barrier layer is applied between the soil and the air, the product in question containing no unprocessed fresh plants or unprocessed fresh plant residues.

It is also surprising that a method of biological soil decontamination that consists of the introduction of an organic particulate product into the soil and the application of a barrier layer between the soil and the air is favourable.

It is also surprising that in particular a method of biological soil decontamination, in which a protein-containing particulate product is introduced into the ground and a barrier layer is applied between the ground and the air gives favourable results.

The method in accordance with embodiments of the invention and its variants ensure a faster and more reliable biological soil decontamination. Biological soil decontamination carried out by the method in accordance with embodiments of the present invention can also lead to a higher yield.

In accordance with embodiments of the present invention, such a product preferably includes a protein-containing material. More preferably, the product contains at least 10 wt-% of protein, calculated on a dry-matter basis, especially at least 15 wt-% of protein, such as at least 20 wt-% of it. In some specific embodiments, the product contains at least 50 wt-% of protein on a dry-matter basis, and especially at least 70 wt-% of protein, in the form of for example wheat gluten or maize gluten.

In accordance with embodiments of the present invention, preferably at least 0.5 gram of protein is introduced per liter of soil, and more preferably at least 1 gram of protein per liter of soil, such as at least 2, at least 4 and especially at least 10 grams of protein per liter of soil. In particular, the amount of protein introduced into the soil per liter of soil is 1-50 g, such as 0.5-50, such as 1-50 g, especially 2-50 g and more especially 4-50 g, such as 4-40 g. The soil decontamination is unsatisfactory if less protein is used, while larger amounts rapidly acidify the soil, thereby inhibiting the decontamination process.

In accordance with embodiments of the present invention, furthermore, the product used only contains a small amount of carbohydrates, especially rapidly degradable carbohydrates, such as carbohydrates including monosaccharides and/or polysaccharides with $\alpha 1 \rightarrow 4$ linkages. The product preferably includes at most 30 wt-% and more preferably at most 20 wt-% of rapidly degradable carbohydrates, calculated on a dry-matter basis. Higher amounts can quickly acidify the soil, inhibiting the process of soil decontamination.

The barrier layer used is preferably essentially impervious to oxygen. A plastic film is used in particular as the barrier layer. In another embodiment, the barrier layer does not include any openings for the plants, so the soil can be virtually fully covered by it. The barrier layer is arranged in particular to create substantially anaerobic conditions in the soil under it. The amount of the product and the nature of the barrier layer are preferably so chosen that—in the course of preferably at least a number of days, such as at least 2 days or at least 5 days—the oxygen content of the air in the soil under the barrier layer is of the order of magnitude of at most 2 vol-% and especially at most 1 vol-%, such as at most 0.5 vol-%. For example, it can drop below about 2 vol-% about 2 days after introduction and coverage, and it can remain the same preferably for at least 2 consecutive days and preferably for at least 5 consecutive days. In one of the embodiments, the barrier layer used preferably has an oxygen transmission rate (OTR) of at most 2000 ml of oxygen per square meter per hour, i.e. an OTR value of at most 2000 ml/m$^2$/h. In a specific embodiment, the OTR value is at most 1500 ml/m$^2$/h. With polyethylene (PE), it is possible to achieve an OTR value of 1400 ml/m$^2$/h, which can create good anaerobic conditions.

DESCRIPTION

With the biological soil decontamination in accordance with the prior art, fresh plants or fresh plant residues, such as, for example, grass cuttings, are introduced into the soil. One of the disadvantages of this is that very variable results are obtained, possibly because of the varying quality and the varying composition of the plant residues introduced into the soil.

With the biological soil decontamination in accordance with embodiments of the present invention, however, it is a well-defined material that is introduced into the soil instead of fresh plants or fresh plant residues.

Embodiments in accordance with the present invention generally relate to a method of biological soil decontamination, in which a product is introduced into the soil, and a barrier layer is applied over the soil, e.g., between the soil and the air. A number of embodiments will be described below for the product to be introduced in the soil and for the method in accordance with embodiments of the invention.

Product Containing a Non-Living Organic Material

Good decontamination results are obtained by the method of biological soil decontamination, in which a product including a non-living organic material is introduced into the soil, and a barrier layer is applied between the soil and the air.

The term "non-living organic material" is used here to denote an organic material that is not in the form of unprocessed plants, plant residues, animals or animal residues, where "unprocessed" means not processed or only subjected to processing that consists of cutting, such as mowing or chopping. Organic materials like grass, straw, leaves, etc. are not covered by the term "non-living organic material". On the other hand, the term does cover organic material obtained by processing plants, animals or parts thereof, where processing entails more than mere cutting; for example, proteins, lipids and carbohydrates that have been isolated are covered by the term. In accordance with embodiments of the present invention, organic materials such as isolated gluten are also covered by this term. In another embodiment, the term also covers organic materials chosen from a group including humus, compost, extracted soya bean meal, bone meal, gelatin and optionally granulated manure. The preferred non-living organic material is non-living biomass.

Embodiments of the invention, therefore, also relate to a method for biological soil decontamination in which a product containing organic material is introduced into the soil, where the said product is chosen from a group including proteins, carbohydrates and lipids and is not in the form of unprocessed plants, plant residues, animals or animal residues, and where the method in question also includes the application of a barrier layer between the soil and the air.

No Un-Processed Fresh Plants or Parts Thereof

In accordance with an advantageous embodiment of the present invention, the method of biological soil decontamination involves the introduction of a product into the soil, where the said product preferably includes a material chosen from a group of proteins, carbohydrates and lipids but does not contain any unprocessed fresh plants or unprocessed fresh plant residues, and where the product preferably includes one or more of the various types of powders, granulates, liquids and agricultural by-products described below, followed by the application of a barrier layer between the soil and the air.

The term "unprocessed fresh plants or unprocessed fresh plant residues" denotes fresh plants or plant residues that have not been subjected to any treatment other than optional cutting, such as mowed grass. The further processing of plants or plant residues can lead for example to products such as extracted rapeseed meal, extracted soya bean meal, gluten, steamed potato peelings and Protamylasse.

The term "agricultural by-product" is used here to denote materials formed in farming and containing proteins and/or carbohydrates and/or lipids, an example being slaughter waste. Other examples of agricultural by-products are extracted soya bean meal, steamed potato peelings and bone meal.

The product preferably includes a material chosen from a group including proteins, carbohydrates and lipids is preferably non-living biomass. The preferred products contain at least 10 wt-% of protein on a dry-matter basis.

Particulate Product

In accordance with an advantageous embodiment of the present invention, the method of biological soil decontamination consist of the introduction of a particulate organic product into the soil, followed by the application of a barrier layer between the soil and the air.

The term "particulate organic material" is used here to denote a particulate product, essentially consisting of particles defined below (such as powders and/or granulates), where the particles contain one or more organic components preferably chosen from a group including proteins, carbohydrates and lipids.

It has also been found that advantageous results are obtained in particular from a method of biological soil decontamination that consists of the introduction of a particulate protein-containing product into the soil and the application of a barrier layer between the soil and the air.

In accordance with another advantageous embodiment of the present invention, the product that is introduced into the soil is therefore in the particulate form. The particles of the product introduced into the ground preferably have a $d_{3,2}$ value of about 0.5 µm to 10 mm, especially about 1 µm to 5 mm, and more especially about 0.1-5 mm. The $d_{3,2}$ value of a particle is defined as the volume/surface area mean surface or Sauter mean diameter.

Powder is a particulate product whose particles can range from very small (for example of the order of magnitude of about 0.5-100 µm) to quite large (for example of the order of magnitude of about 0.1-1 mm). In the case of a granulate, the particle size can vary for example from about 1 to 10 mm. According to one of the advantageous embodiments of the present invention, the product introduced into the soil is a granulate. According to another advantageous embodiment of the present invention, the product introduced into the soil is a powder.

Liquid or Slurry

In accordance with another advantageous embodiment of the present invention, the product to be introduced into the soil includes a liquid.

The term "liquid" is used here to denote a pourable substance including one or more components. The person skilled in the art will realize that a liquid can be for example an emulsion, dispersion, solution, aqueous slurry, suspension and the like. An example of the liquids that can be used in the method in accordance with embodiments of the present invention is milk, such as cow's, calf's, goat's milk, etc.

In accordance with another advantageous embodiment of the present invention, the liquid or slurry preferably contains at least 10 wt-% of proteins, calculated on a dry-matter basis.

In accordance with another advantageous embodiment of the present invention, the liquid or slurry contains at least 10 wt-% of protein and/or at most 90 wt-% of carbohydrates and/or at most 90 wt-% of lipids, on a dry-matter basis, totaling 100 wt-%.

In accordance with embodiments, the liquid or slurry includes at least 1 wt-% of carbohydrates and/or lipids on a dry-matter basis, totaling 100 wt-%. If the liquid or slurry contains protein in combination with carbohydrates and/or lipids, then the total amount of carbohydrates and lipids in wt-% is preferably less than about ten times the amount of protein in wt-%.

In accordance with another advantageous embodiment of the present invention, the product to be introduced into the soil includes a slurry, such as, for example, an aqueous slurry of one or more of the following substances: wheat gluten, thick potato sap, Protamylasse, wheat yeast concentrate and liquid by-products of bio-ethanol production.

General

The product, notably the product including non-living organic material, the product including no unprocessed fresh plants or unprocessed fresh plant parts, the particulate organic product, or the particulate protein-containing product, preferably contains one or more organic components (materials) chosen from a group including proteins, carbohydrates and lipids (where the particulate protein-containing product contains proteins by definition), for example a combination (mixture) of proteins or a combination (mixture) of proteins and binders, or combinations of one or more proteins, carbohydrates and inorganic substances.

In accordance with another advantageous embodiment of the present invention, this product includes at least 10 wt-% of organic components, for example 60-100 wt-% of organic components, such as proteins and/or carbohydrates and/or lipids, and preferably in any case at least 10 wt-% of proteins and/or at most 90 wt-% of carbohydrates and/or at most 90 wt-% of lipids, all on a dry-matter basis, totaling 100 wt-%.

In accordance with embodiments, the liquid includes at least 1 wt-% of carbohydrates and/or lipids on a dry-matter basis, totaling 100 wt-%. If the product contains protein in combination with carbohydrates and/or lipids, then the total amount of carbohydrates in wt-% is preferably less than about ten times the amount of protein in wt-%.

Proteins

Suitable proteins are exemplified by potato protein, Protamylasse, bone meal and gluten. In one of the embodiments, the term "protein" also covers a combination of proteins. Gluten forms a specific group of proteins, occurring in some seeds and grains.

In accordance with embodiments of the present invention, the product to be introduced into the soil preferably includes the particulate or liquid protein-containing product, gluten. Moreover, in accordance with another advantageous embodiment of the present invention, the product to be introduced into the soil preferably includes a particulate or liquid protein-containing product chosen from wheat gluten, maize gluten and a combination thereof.

In accordance with embodiments, the product to be introduced into the soil includes other proteins, such as, for example, potato protein, soya bean protein, bone meal or a combination thereof.

In accordance with embodiments, the product to be introduced into the soil includes a combination of glutens, such as for example wheat gluten, maize gluten or a combination thereof, and other proteins, such as for example potato protein, soya bean protein, bone meal or a combination thereof.

In accordance with another advantageous embodiment of the present invention, the product to be introduced into the soil includes especially a particulate or liquid product in the form of one or more proteins, with preferably at least about 10 wt-% of protein (on a dry-matter basis), for example with 10-30 wt-% of protein.

In accordance with another advantageous embodiment of the present invention, the product to be introduced into the soil is therefore a protein-containing, preferably particulate or liquid, product. The term "protein-containing particulate or liquid product" denotes here a product that both contains protein and is particulate, such as for example a powder or a granulate, or it is a liquid, such as for example an aqueous slurry.

In accordance with embodiments, the proteins that are preferred are chosen from a group including potato protein, wheat protein and microbial protein.

A suitable form of protein-containing non-living organic material is Protamylasse, which is a liquid. Another suitable form of protein-containing non-living organic material is Protapec. Protamylasse (or thick potato sap) is one of the products obtained in the processing of starch potatoes. It is mixed with soya husks and then dried. The granulate obtained in this way is called Protapec, which is available from the Avebe Company in the Netherlands. Another suitable form of protein-containing non-living organic material is wheat gluten. Yet another suitable form of protein-containing non-living organic material is a product that contains microbial protein. The term "microbial protein" denotes a protein that is obtained from fermentation processes. An example of products containing microbial proteins is wheat yeast concentrate, which is obtained from the fermentation of wheat. Microbial protein can also be formed in the fermentation of for example maize, etc. One can, therefore, use for example wheat yeast concentrate and/or maize yeast concentrate as the protein-containing non-living organic material.

Introduction into the Soil

The product is introduced into the soil and preferably into the top layer of the soil, that is to say, down to a depth of about 50 cm. The product can be introduced by ploughing it into the soil, but it can also be injected into the soil. The term "introduction into the soil" and similar expressions used here denote notably the introduction of the product into the soil by man, possibly with the aid of machines.

In accordance with another advantageous embodiment of the present invention, 1-50 g of proteins are introduced per liter of soil, 1-100 g of carbohydrates are introduced per liter of soil, and 1-100 g of lipids are introduced into the soil. If proteins are used in combination with carbohydrates and/or lipids, then the total amount of carbohydrates and lipids in wt-% is preferably less than about ten times the amount of proteins in wt-%.

Barrier Layer

In order to create the anaerobic conditions in the soil that are advantageous for biological soil decontamination, a barrier layer is applied between the soil and the air after the introduction of the product described above. The term "application of a barrier layer between the soil and the air" covers various options and denotes in particular the placement of a barrier layer on the ground, i.e., generally in contact with the soil, but it also includes cases where the top layer of the soil is worked, for example, by compaction.

In accordance with another advantageous embodiment of the present invention, the barrier layer is made of a plastic. Here, the term "plastic" also covers film materials. When biological soil decontamination is effected by the introduction of plants or plant residues into the soil, an expensive plastic film with a very low oxygen permeability (transmission) is needed to create the required anaerobic conditions and to retain these conditions for the time needed for effective decontamination to take place (generally 6 weeks).

In accordance with another advantageous embodiment of the present invention, however, biological soil decontamination can be effected in a shorter period, partly because the amount of oxygen in the soil decreases here very quickly (the required oxygen-free state is reached within 2 days), and partly because the products introduced into the soil are in a very readily accessible form, so they can be quickly digested. Since the anaerobic conditions have to be maintained for a shorter time (for example, 2 weeks) in the biological soil decontamination according to the present invention, a cheaper, less air-tight alternative to the expensive air-tight film can be used. The plastics and films that can be used to apply a barrier layer between the soil and the air are exemplified by low-density polyethylene (LDPE), high-density polyethylene (HDPE), nylon, multi-ply barrier film (such as Hytibarrier film), biodegradable film and plastics, as well as spray-on plastics or other spray-on film-forming products.

Under certain conditions, it may be possible to create a barrier layer between the soil and the air by rolling the top layer of the soil or driving over it in order to compress or compact it and therefore seal it. In accordance with another advantageous embodiment of the present invention, the barrier layer is, therefore, applied between the soil and the air by compacting the top layer of the soil.

Another possible alternative for the application of a barrier layer between the soil and the air is sealing the soil with water. In accordance with another advantageous embodiment of the present invention, the barrier layer is applied by inundation. The barrier layer is preferably applied 0-72 hours, and preferably 0-48 hours after the introduction of the product into the soil. It can be removed, if required, preferably about 1-6 weeks, especially 1-4 weeks and more especially 2-3 weeks after it is applied.

The method in accordance with embodiments of the present invention is preferably employed without placing any plants in the soil between the introduction of the product into the soil and the application of the barrier layer. The method in accordance with embodiments of the present invention is preferably employed without the presence of any plants to be grown and/or cultivated during the introduction of the product into the soil.

Miscellaneous

Without wishing to be bound to a theory, we would note that the explanation for the excellent results obtained in the biological soil decontamination in accordance with embodiments of the present invention seems to be that the products introduced into the soil undergo rapid fermentation, so the soil becomes anaerobic more quickly. In addition, the resulting oxygen-free state is more satisfactory and/or persists for longer. This may be due to the high biological oxygen demand (BOD) of the products used. The BOD value is a measure of the amount of oxygen consumed by the microorganisms when degrading an organic material. If a product has a high BOD value, a large amount of oxygen is consumed during its degradation, and the anaerobic conditions needed for soil decontamination are ensured quickly and effectively.

Furthermore, the decomposition products formed in the anaerobic degradation of the products introduced into the soil, such as for example methane ($CH_4$), carbon monoxide (CO) and hydrogen sulphide ($H_2S$), also seem to play an important role in the destruction of the harmful organisms present in the soil. It seems that a larger amount and/or more effective kinds of these decontaminating substances are released in the present method than in the conventional method involving the use of fresh plant residues.

One of the advantages of the method in accordance with embodiments of the present invention is that the product that is introduced into the soil can have a known and, furthermore, a constant composition. In addition, the product is preferably particulate or liquid, which ensures its easy and uniform distribution in the soil.

Another advantage is that the biological soil decontamination in accordance with embodiments of the present invention can also be carried out either in early spring or in the autumn, since the soil temperature is less important here than in the case of biological decontamination by the introduction of fresh plant residues into the soil, and biological soil decontamination in accordance with embodiments of the present invention also gives good results at lower temperatures. Moreover, it is no longer necessary to cultivate the plant that is to be ploughed in, so weeks or even months can be spared.

Example 1

The effectiveness of various products was tested in the biological soil decontamination carried out in accordance with embodiments of the present invention. Sandy soil was contaminated with the northern root knot nematode and placed in buckets with a capacity of 3 liters. Various products were introduced into the soil, and a barrier layer was applied between the soil and the air. The oxygen consumption and the methane production in the soil, and/or the destruction of the nematodes were determined. The results are summarized in Table 1, which illustrates the effectiveness of various products in biological soil decontamination in accordance with embodiments of the present invention.

TABLE 1

| Product | Grams of protein per litre of soil | Grams of product per litre of soil | Oxygen consumption[1] | Methane production[1] | Destruction of nematodes, %[2] |
|---|---|---|---|---|---|
| Maize gluten meal | 25.50 | 153 | | | 100 |
| Maize gluten meal | 6.30 | 38 | | | 100 |
| Maize gluten meal | 1.20 | 7 | good | good | 100 |
| Wheat gluten | 4.80 | 7 | very good | very good | 100 |
| Wheat gluten | 2.40 | 3 | good | good | 100 |
| Protamylasse | 17.15 | 86 | | | 100 |
| Protamylasse | 6.52 | 33 | very good | very good | 100 |
| Maize gluten | 3.83 | 7 | very good | very good | 100 |
| Rapeseed cake | 4.20 | 12 | reasonable | reasonable | |
| Calf's milk | 2.40 | 11 | good | reasonable | |
| Granular chicken manure | 1.80 | 12 | very good | very good | |

[1] The oxygen consumption and the methane production are expressed here in qualitative terms. They were determined twice a day for a number of weeks, and the overall picture was rated qualitatively as very good, good, reasonable, moderate or minimal.
[2] The percentage of surviving nematodes was determined 2 weeks after closing the bucket. The percentage of nematode destruction was calculated from the percentage of surviving nematodes.

It holds in general that when the oxygen consumption is high, the methane production is also high. This means that a satisfactory anaerobic decomposition is taking place, and the nematode destruction rate is high in these cases. The products given in Table 1 as examples are all high-protein substances; in all these cases, the oxygen consumption and the methane production were either good or very good, and the nematode destruction rate was 100%.

Example 2

In this comparative example, the effectiveness of the various fresh plant residues in biological soil decontamination was determined. Sandy soil was contaminated with the northern root knot nematode and placed in buckets with a capacity of 3 liters. Various plant residues were then introduced into the soil, and a barrier layer was applied between the soil and the air. The oxygen consumption and the methane production in the soil, and/or the destruction of the nematodes were determined. The results are summarized in Table 2, which illustrates the effectiveness of various plant residues in biological soil decontamination.

TABLE 2

| Product | Grams of protein per litre of soil | Grams of product per litre of soil | Oxygen consumption[1] | Methane production[1] | Destruction of nematodes, %[2] |
|---|---|---|---|---|---|
| Lawn grass | 0.48 | 13.6 | | | 95 |
| Lawn grass | 0.30 | 8.5 | | | 15 |
| Grass | 0.24 | 6.8 | little | minimal | 0 |

[1] The oxygen consumption and the methane production are expressed here in qualitative terms. They were determined twice a day for a number of weeks, and the overall picture was rated qualitatively as very good, good, reasonable, moderate or minimal.
[2] The percentage of surviving nematodes was determined 2 weeks after closing the bucket. The percentage of nematode destruction was calculated from the percentage of surviving nematodes.

The results listed in Table 2 show that when the protein content of the plants introduced into the soil is low, the oxygen consumption and the methane production are also low. In these cases, the destruction of the nematodes is poor. Grass, which is the usual plant employed in biological soil contamination, contains a relatively small amount of protein, and when grass is introduced into the soil, only a small amount of oxygen is consumed, the methane production is low, and the destruction of nematodes is poor.

Example 3

Table 3 shows the data for a number of suitable and less suitable non-living organic materials as examples. Table 3 particularly illustrates the effectiveness of various non-living organic materials in biological soil decontamination The amount of proteins introduced into the soil with some of the non-living organic material was also varied here.

TABLE 3

| Material | Protein content (on dry-matter basis) | Grams of material per litre of soil | Grams of protein per litre of soil | Destruction | Contaminant |
|---|---|---|---|---|---|
| Wheat gluten | >80% | 3 | 2.4 | v.g. | Nematodes |
| Wheat gluten | >80% | 5 | 4 | v.g. | Nematodes |
| Wheat gluten | >80% | 7 | 4.8 | v.g. | Nematodes |
| Wheat gluten | >80% | 10 | 8 | v.g. | Nematodes |
| Wheat gluten | >80% | 20 | 16 | v.g. | Nematodes |
| Maize gluten | 64% | 10 | 6 | v.g. | Nematodes |
| Maize gluten fodder meal | 37% | 153 | 25.5 | v.g. | Nematodes |
| Maize gluten fodder meal | 37% | 38 | 6.3 | v.g. | Nematodes |
| Maize gluten fodder meal | 37% | 7 | 1.2 | v.g. | Nematodes |
| Protamylasse | 34% | 86 | 17.2 | v.g. | Nematodes |
| Protamylasse | 34% | 33 | 6.5 | v.g. | Nematodes |
| Wheat yeast concentrate | 35% | 6 | 2 | v.g. | Verticillium, nematodes |
| Protapec | 21% | 10 | 2 | v.g. | Verticillium + Fusarium + nematodes |
| Protapec | 21% | 20 | 4 | v.g. | Verticillium + Fusarium + nematodes |
| Protapec | 21% | 30 | 6 | v.g. | Verticillium + Fusarium + nematodes |
| Protamylasse | 34% | 15 | 3 | v.g. | Nematodes |
| Protamylasse | | 30, 50 | 6, 10 | v.g. | Nematodes |
| Potato cell walls | 5% | 5 | 0.25 | p. | Nematodes |
| Potato cell walls | | 10, 20, 40 | 0.5, 1, 2 | g. | Nematodes |
| Wheat flour | 15% | 5 | 0.75 | p. | Nematodes |
| Wheat flour | 15% | 10, 20, 40 | 1.5, 3, 6 | v.g. | Nematodes |
| Barley granules | 10% | 5, 10 | 0.5, 1.0 | p. | Nematodes |
| Barley granules | 10% | 20, 40 | 2, 4 | g. | Nematodes |
| Wheat starch | <5% | 5, 10, 20, 40 | <1 | p. | Nematodes |
| Potato starch | <5% | 5, 10, 20, 40 | <1 | p. | Nematodes |
| Lawn grass | <10% | 8.5 | 0.3 | p. | Nematodes |
| Grass | <10% | 6.8 | 0.24 | p. | Nematodes |

TABLE 3-continued

| Material | Protein content (on dry-matter basis) | Grams of material per litre of soil | Grams of protein per litre of soil | Destruction | Contaminant |
|---|---|---|---|---|---|
| Grass | <10% | 16, 20 | <1 | p. | Nematodes |
| Grass | <10% | 32 | 1 | moderate | Nematodes |
| Wheat gluten without a cover | | 2  4  8 | | poor | Nematodes | v.g.: very good
g.: good
p.: poor
Nematodes = northern root knot nematodes
Without a cover = no cover was applied at all (nor was the top layer compressed, etc.)

Example 4

The results described hereinbelow were obtained with soya meal and other high-protein and low-protein substances. These studies were carried out with the following products: Three high-protein products: soya bean meal, extracted soya bean meal, and Protapec in various amounts. The first two products, both of which contained 46% of protein on a dry-matter basis, had been obtained from Hendrix UTD in the Netherlands, and the third one, which contained 21% of protein on a dry-matter basis had been acquired from Jelle de Vries BV, also in the Netherlands. In two further series, the protein was used in an amount of 1 and 4 grams per liter of soil, with various added amounts of maize starch, representing 100% of carbohydrate.

These studies were carried out in a poor sandy soil, containing little organic matter. The soil was covered with a plastic film after the introduction of the materials into it. The quality of the anaerobic conditions was then determined. The destruction was low when the conditions were not sufficiently anaerobic, i.e. when the oxygen content did not drop below 2% for a period of a number of days. When there was a period during which the oxygen content was below 2% for at least a number of days, the nematode destruction was generally 100%.

Results

The reduction of the oxygen content was the best (i.e., the lowest, the quickest and the most enduring) when the amount of protein introduced was between 4 and 40 grams per liter of soil in the case of all 3 materials. When the amount of protein was reduced to below 0.5 gram per liter of soil, the oxygen reduction rapidly dropped, and the same happened when the amount of protein was raised above 40 grams per liter of soil.

When no protein was introduced (i.e. when only maize starch was used), the reduction in the amount of oxygen was virtually zero, so the conditions were not anaerobic. When the amount of protein introduced was 1 or 4 grams per liter of soil, the degree of anoxia, and so the rate of destruction were less if carbohydrates were added, and decreased further as more and more carbohydrates were added in the form of starch. When only carbohydrates were used (i.e. when the amount of proteins was zero gram per liter of soil), virtually no methane was formed.

The methane formation was higher with soya products than with Protapec, probably because they contained more lipids. The methane formation also had an optimum, so too much material inhibits the decomposition.

Although embodiments have been described herein, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method for biological soil decontamination comprising:
   introducing a product containing non-living organic material to the soil, wherein said product comprises protein, wherein said protein is introduced in an amount of 0.5-50 grams per liter of soil; and then
   applying a barrier layer between the soil and air.

2. The method of claim 1, wherein said product comprises one or more proteins chosen from the group consisting of potato protein, wheat protein and microbial protein.

3. The method of claim 1, wherein said product contains at least 10 wt-% of protein, calculated on a dry-matter basis.

4. The method of claim 1, wherein said product contains at least 20 wt-% of protein, calculated on a dry-matter basis.

5. The method of claim 1, wherein the amount of said protein introduced into the soil is at least 2 grams per liter of soil.

6. The method of claim 1, wherein the amount of said protein introduced into the soil is 4-50 grams.

7. The method of claim 1, wherein the amount of said protein introduced into the soil is 4-40 grams per liter of soil.

8. The method of claim 1, wherein the amount of said protein introduced into the soil is at least 10 grams per liter of soil.

9. The method of claim 1, wherein said product comprises one of:
   wheat protein;
   wheat gluten;
   potato protein;
   Protamylasse; and
   microbial protein.

10. The method of claim 1, wherein said product comprises at least one of:
    wheat yeast concentrate; and
    maize yeast concentrate.

11. The method of claim 1, wherein said product is one of:
    a particulate;
    a liquid; and a slurry.

12. The method of claim 1, wherein said product is low on rapidly degradable carbohydrates.

13. A method for biological soil decontamination comprising:
   introducing a particulate product into the soil, wherein said particulate product contains protein, wherein said protein is introduced in an amount of 0.5-50 grams per liter of soil; and then
   applying a barrier layer over the soil.

14. The method of claim 13, wherein said product comprises one of:
   a granulate; and
   a powder.

15. The method of claim 13, wherein said product includes particles with a $d_{3,2}$ value in the range of 0.5 μm-10 mm.

16. The method of claim 13, wherein said product includes particles with a $d_{3,2}$ value in the range of 1 μm-5 mm.

17. The method of claim 13, wherein said product includes particles with a $d_{3,2}$ value in the range of 0.1-5 mm.

18. The method of claim 13, wherein said product contains gluten.

19. The method of claim 13, wherein said barrier layer comprises one of:
   a plastic; and
   a spray-on film-forming material.

20. The method of claim 13, wherein said barrier layer is applied by one of:
   compacting the top layer of the soil; and
   inundation.

21. The method of claim 13, wherein said barrier layer has an oxygen transmission rate (OTR) of no more than 2000 ml of oxygen per square meter per hour.

* * * * *